(12) United States Patent
Cederschiöld et al.

(10) Patent No.: US 9,895,290 B2
(45) Date of Patent: Feb. 20, 2018

(54) MECHANICAL FRICTION ENHANCEMENT FOR THREADED CONNECTION INCORPORATING OPPOSING BARB

(71) Applicant: Becton Dickinson and Company Ltd., Dun Laoghaire (IE)

(72) Inventors: Alexander Cederschiöld, Gothenburg (SE); Angela Gilbert, Elmwood Park, NJ (US); Christopher Carney, Clinton, NJ (US)

(73) Assignee: Becton Dickinson and Company Ltd., Dun Laoghaire (IE)

( * ) Notice: Subject to any disclaimer, the term of this patent is extended or adjusted under 35 U.S.C. 154(b) by 829 days.

(21) Appl. No.: 14/278,876

(22) Filed: May 15, 2014

(65) Prior Publication Data
US 2014/0339813 A1    Nov. 20, 2014

Related U.S. Application Data

(60) Provisional application No. 61/824,163, filed on May 16, 2013.

(51) Int. Cl.
*A61M 39/10*    (2006.01)
*A61J 1/20*    (2006.01)

(52) U.S. Cl.
CPC ........ *A61J 1/2096* (2013.01); *A61M 39/1011* (2013.01); *A61M 2039/1033* (2013.01); *A61M 2039/1044* (2013.01); *Y10T 29/49948* (2015.01)

(58) Field of Classification Search
CPC ...... A61M 39/1011; A61M 2039/1077; A61M 2039/1033; A61M 2039/1044
See application file for complete search history.

(56) References Cited

U.S. PATENT DOCUMENTS

| | | | |
|---|---|---|---|
| 3,405,831 A | 10/1968 | Hudson | |
| 3,876,234 A | 4/1975 | Harms | |
| 4,360,024 A | 11/1982 | Wallace | |
| 4,452,473 A | 6/1984 | Ruschke | |
| 4,519,518 A * | 5/1985 | Wiles | B65D 41/0414 215/331 |
| 4,629,455 A * | 12/1986 | Kanno | A61M 5/344 285/332 |
| 4,735,441 A | 4/1988 | Stephens | |

(Continued)

FOREIGN PATENT DOCUMENTS

| | | |
|---|---|---|
| EP | 0158030 A1 | 10/1985 |
| EP | 2174687 A2 | 4/2010 |

(Continued)

*Primary Examiner* — Nathan R Price
*Assistant Examiner* — Melissa A Snyder
(74) *Attorney, Agent, or Firm* — The Webb Law Firm

(57) ABSTRACT

A medical connector includes a body having a distal end, a proximal end, and a sidewall extending between the distal end and the proximal end. The medical connector further includes a helical thread extending radially outward from a surface of the sidewall and at least one protrusion extending radially outward from a surface of the sidewall. The at least one protrusion has a first side and a second side. A radial height of the at least one protrusion from the surface of the sidewall tapers circumferentially from the first side of the at least one protrusion to the second side of the at least one protrusion.

21 Claims, 7 Drawing Sheets

(56) References Cited

U.S. PATENT DOCUMENTS

| | | | |
|---|---|---|---|
| 5,112,318 A * | 5/1992 | Novacek | A61L 2/28 604/195 |
| 5,176,415 A | 1/1993 | Choksi | |
| 5,213,225 A | 5/1993 | King et al. | |
| 5,263,945 A | 11/1993 | Byrnes et al. | |
| 5,312,377 A | 5/1994 | Dalton | |
| 5,591,143 A | 1/1997 | Trombley, III et al. | |
| 5,620,427 A | 4/1997 | Werschmidt et al. | |
| 5,651,776 A | 7/1997 | Appling et al. | |
| 5,676,270 A | 10/1997 | Roberts | |
| 5,702,374 A | 12/1997 | Johnson | |
| 5,855,568 A | 1/1999 | Battiato et al. | |
| 5,871,473 A | 2/1999 | Strauss et al. | |
| 5,984,373 A | 11/1999 | Fitoussi et al. | |
| 6,074,373 A | 6/2000 | Sudo et al. | |
| 6,152,913 A | 11/2000 | Feith et al. | |
| 6,224,588 B1 * | 5/2001 | Jentzen | A61M 5/347 604/241 |
| 6,673,059 B2 | 1/2004 | Guala | |
| 6,722,705 B2 | 4/2004 | Korkor | |
| 6,843,513 B2 | 1/2005 | Guala | |
| 6,869,426 B2 | 3/2005 | Ganem | |
| 6,893,056 B2 | 5/2005 | Guala | |
| 7,128,348 B2 | 10/2006 | Kawamura et al. | |
| 7,314,061 B2 | 1/2008 | Peppel | |
| 7,347,458 B2 | 3/2008 | Rome et al. | |
| 7,503,596 B2 | 3/2009 | Rome et al. | |
| 7,523,967 B2 | 4/2009 | Steppe | |
| 7,618,072 B2 | 11/2009 | Funamura et al. | |
| 7,708,714 B2 | 5/2010 | Connell et al. | |
| 7,722,090 B2 | 5/2010 | Burton et al. | |
| 7,740,288 B2 | 6/2010 | Mantell | |
| 7,998,133 B2 | 8/2011 | Fago et al. | |
| 7,998,134 B2 | 8/2011 | Fangrow et al. | |
| 8,038,182 B2 | 10/2011 | Kurimoto et al. | |
| 8,162,897 B2 | 4/2012 | Byrum | |
| 8,262,644 B2 | 9/2012 | Fago et al. | |
| 8,286,936 B2 | 10/2012 | Kitani et al. | |
| 8,287,518 B2 | 10/2012 | Kitani et al. | |
| 8,372,057 B2 | 2/2013 | Cude et al. | |
| 8,372,059 B2 | 2/2013 | Ziman | |
| 9,233,772 B2 * | 1/2016 | Kuzma | B65D 1/0246 |
| 2003/0073959 A1 | 4/2003 | Koska | |
| 2004/0238776 A1 | 12/2004 | Peters et al. | |
| 2008/0004600 A1 | 1/2008 | Kitani et al. | |
| 2008/0103485 A1 | 5/2008 | Kruger | |
| 2008/0140020 A1 | 6/2008 | Shirley | |
| 2008/0140055 A1 | 6/2008 | Shirley | |
| 2008/0287919 A1 | 11/2008 | Kimball | |
| 2008/0314856 A1 * | 12/2008 | Penny | B29C 49/06 215/252 |
| 2009/0143746 A1 | 6/2009 | Mudd et al. | |
| 2009/0163859 A1 | 6/2009 | Lloyd et al. | |
| 2009/0177186 A1 | 7/2009 | Delano | |
| 2009/0187166 A1 | 7/2009 | Young | |
| 2009/0243281 A1 * | 10/2009 | Seifert | A61M 39/1011 285/38 |
| 2010/0022951 A1 | 1/2010 | Ferrera et al. | |
| 2010/0036365 A1 | 2/2010 | Becker | |
| 2010/0089475 A1 | 4/2010 | Tracey | |
| 2010/0094260 A1 | 4/2010 | Cude et al. | |
| 2010/0152669 A1 | 6/2010 | Rosenquist | |
| 2010/0283238 A1 | 11/2010 | Deighan et al. | |
| 2011/0095528 A1 | 4/2011 | Forberg | |
| 2011/0165020 A1 | 7/2011 | Tryggvason et al. | |
| 2012/0041425 A1 | 2/2012 | Tsunematsu et al. | |
| 2012/0116355 A1 | 5/2012 | Heinz et al. | |
| 2012/0209252 A1 | 8/2012 | Nikitina et al. | |
| 2013/0046255 A1 | 2/2013 | Ziman et al. | |
| 2013/0069365 A1 | 3/2013 | Pokorney | |
| 2013/0076030 A1 | 3/2013 | Fog et al. | |
| 2013/0079754 A1 | 3/2013 | Sheffer | |
| 2013/0103003 A1 | 4/2013 | Capitaine et al. | |

FOREIGN PATENT DOCUMENTS

| | | |
|---|---|---|
| GB | 2353078 A | 2/2001 |
| GB | 2379253 A | 3/2003 |
| JP | 5506416 A | 9/1993 |
| JP | 200372793 A | 3/2003 |
| JP | 2005466 A | 1/2005 |
| WO | 2008144447 A2 | 11/2008 |

* cited by examiner

MECHANICAL FRICTION ENHANCEMENT FOR THREADED CONNECTION INCORPORATING OPPOSING BARB

CROSS-REFERENCE TO RELATED APPLICATION

This application claims priority to U.S. Provisional Application Ser. No. 61/824,163, filed May 16, 2013, which is hereby incorporated by reference in its entirety.

BACKGROUND OF THE INVENTION

Field of the Invention

The present invention relates to a connector for enabling fluid transfer between a first fluid container and a second fluid container. More specifically, the invention is directed to a connector having structure to increase friction between threaded connection portions.

Description of Related Art

Many medical connectors comprise a first component having a female luer-lock element that is arranged to be rigidly joined to a corresponding male luer-lock element of a second connector component that is attached to a medical line or other medical connection, for example. The male luer-lock element can, thus, be freely screwed into and unscrewed from the female luer-lock element. However, once the male luer-lock element has been screwed into the female luer-lock element of the connector, there is a risk that the connector components may be accidentally or inadvertently unscrewed, which could lead to the disconnection of the fluid passage. This may entail a serious contamination risk for a patient and/or any other person in the vicinity of the disconnected medical connector. Such a disconnection risk must especially be avoided when administering toxic fluid, such as cytostatic agents.

In addition, when the friction between the female luer-lock and the male luer-lock is low, there is a tendency for users to over-torque the connection because there is no discernable indication that the connection has been fully tightened. This can lead to breakage of the connectors and/or the containers being joined. This low friction is common for connectors used when administering toxic fluid, such as cytostatic agents for chemotherapy, as such connectors are generally made from plastic or polymeric materials whose hardness and/or surface characteristics result in surfaces having low coefficients of friction.

It is, therefore, desirable to provide a connection for enabling fluid transfer between a first fluid container and a second fluid container that provides not only some resistance to disconnection, but also an indication to the user when the connection begins engagement.

SUMMARY OF THE INVENTION

In one embodiment, a medical connector includes a body having a distal end, a proximal end, and a sidewall extending between the distal end and the proximal end. The medical connector further includes a helical thread extending radially outward from a surface of the sidewall and at least one protrusion extending radially outward from a surface of the sidewall. The at least one protrusion has a first side and a second side. A radial height of the at least one protrusion from the surface of the sidewall tapers circumferentially from the first side of the at least one protrusion to the second side of the at least one protrusion.

A circumferential width of the at least one protrusion may increase as a distance from the distal end of the connector to the at least one protrusion increases. The helical thread may be superimposed over the at least one protrusion, and the at least one protrusion may be a vertical rib. The vertical rib may have a proximal end and a distal end, with the vertical rib having a circumferential width that tapers axially from the proximal end of the vertical rib where the at least one vertical rib has the widest circumferential width to the distal end of the vertical rib where the at least one vertical rib has the narrowest circumferential width. The second side of the protrusion may be substantially flush with the sidewall. A maximum radial height of the at least one protrusion from the surface of the sidewall of the connector may be less than a radial height of the at least one helical thread of the connector from the sidewall. A radial height of the at least one protrusion from the surface of the sidewall of the connector may increase as a distance from the distal end of the connector increases.

The medical connection may further include a stop extending radially outward from the surface of the sidewall at the proximal end of the connector. A radial height of the stop from the sidewall may taper circumferentially from a first end to a second end of the stop such that the first end of the stop has a radial height from the surface of the sidewall that is larger than a radial height of the second end from the surface of the sidewall. A second end of the stop may be adjacent a proximal-most end of the helical thread. The at least one protrusion may be a vertical rib having a proximal end and a distal end, and the helical thread may include first and second helical ribs, with the vertical rib extending through the first and second helical ribs. The vertical rib may be divided into a plurality of sections by the first and second helical ribs of the helical thread.

In a further embodiment, a medical connector includes a body having a distal end, a proximal end, and a sidewall extending between the distal end and the proximal end. The medical connector also includes a helical thread extending radially outward from a surface of the sidewall and at least one protrusion extending radially outward from a surface of the sidewall. The at least one protrusion has a proximal end and a distal end. A circumferential width of the at least one protrusion is larger at the proximal end of the at least one protrusion than the circumferential width of the at least one protrusion at the distal end of the at least one protrusion.

The circumferential width of the at least one protrusion may increase as a distance from the distal end of the connector to the at least one protrusion increases. The helical thread may be superimposed over the at least one protrusion, and the at least one protrusion may be a vertical rib. A maximum radial height of the at least one protrusion from the surface of the sidewall of the connector is less than a radial height of the at least one helical thread of the connector from the sidewall. A radial height of the at least one protrusion from the surface of the sidewall of the connector may increase as a distance from the distal end of the connector increases.

In another embodiment, a method of connecting two fluid containers includes: providing a connector having a helical thread extending radially outward from a surface of the connector, and a mating connector comprising a helical thread extending radially outward from a surface of the mating connector with the connector including at least one protrusion extending radially outward from the surface of the connector; engaging the helical thread of the mating connector with the helical thread of the connector; advancing the mating connector onto the connector by rotating the mating connector; and engaging the at least one protrusion with the mating connector such that the friction between the connector and the mating connector is increased when the at least one protrusion of the connector contacts the helical thread of the mating connector as the mating connector is advanced onto the connector. The at least one protrusion is sized and positioned such that the increase in friction provided by contact with each successive portion of the protrusion is greater than the increase in friction provided by a previously contacted portion of the protrusion.

A first portion of the at least one protrusion that first contacts the helical thread of the mating connector may have a narrower circumferential width than a second portion of the at least one protrusion that is subsequently contacted by the helical thread of the mating connector as the mating connector is advanced on the connector. A first portion of the at least one protrusion that first contacts the helical thread of the mating connector may have a maximum radial height from a surface of the connector that is smaller than a maximum radial height from a surface of the connector of a second portion of the at least one protrusion that is subsequently contacted by the helical thread of the mating connector as the mating connector is advanced onto the connector. The method may further include engaging a stop with the mating connector to stop advancement of the mating connector onto the connector.

DESCRIPTION OF THE INVENTION

Figure 1:
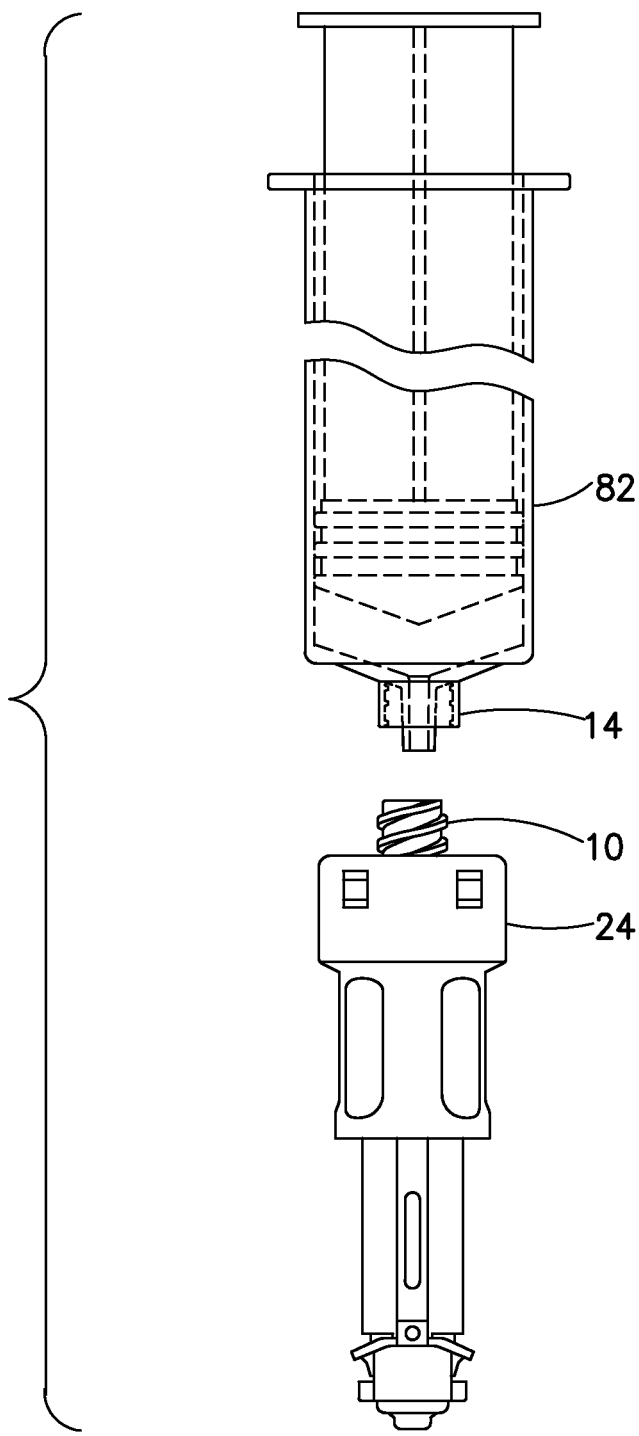
FIG. 1 is a perspective view of a conventional syringe and syringe adapter.
Figure 2:
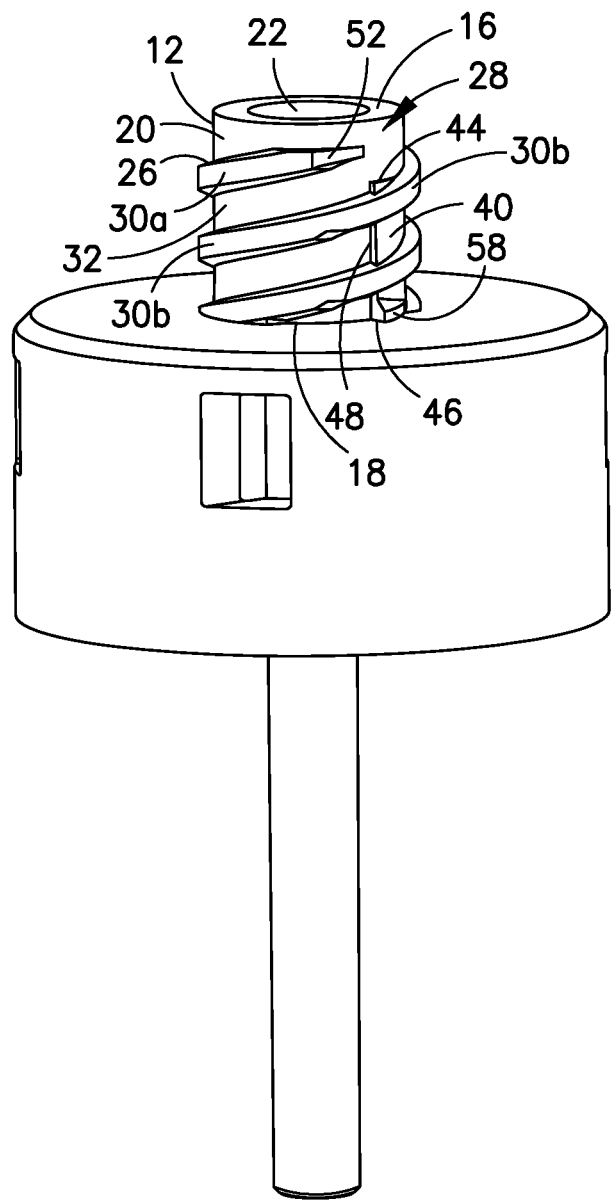
FIG. 2 is a front perspective view of a connector according to one embodiment of the present application.

For purposes of the description hereinafter, the terms such as "end", "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting. Further, it is to be understood that the invention may assume various alternative variations and step sequences, except where expressly specified to the contrary.

Referring to FIG. 1, a conventional syringe 82 and syringe adapter 24 are shown. The syringe 82 includes a male luer-lock connector that is configured to be secured to a corresponding female luer-lock connector of the syringe adapter 24. The syringe adapter 24 may be a BD PhaSeal™ Injector commercially available from Becton, Dickinson and Company. The syringe adapter 24 forms part of a closed system transfer device that enables a closed transfer of drugs between containers.

One embodiment of the present invention is directed to a connector 10 for fluidly connecting a first fluid container to a second fluid container to allow the fluid in one of the first or second fluid container to pass into the other of the first or second fluid container. For example, the connector 10 may be utilized in connection with the syringe adapter 24 shown in FIG. 1. A "fluid container" as used in herein is intended to mean any vessel that can at least temporarily contain a fluid, including, but not limited to, a vial, a medical line, a tube, or an infusion fluid container, such as an infusion bottle or an infusion bag, a syringe, or other device.

As shown in FIGS. 2-7, the connector 10 includes a body 12 having a distal end 16, a proximal end 18, and a sidewall 20 extending between the distal end 16 and the proximal end 18 and defining a central lumen 22. The sidewall 20 may be generally cylindrical. The connector 10 may be a female luer-lock connector, although other suitable connector arrangements may be utilized. The proximal end 18 of the body 12 of the connector 10 may be attached directly to a first fluid container or may extend from an additional connection portion that connects directly to the fluid container to provide a fluid connection between the first fluid container and the central lumen 22 of the connector 10. In the embodiment shown in FIGS. 2-7, the body 12 of the connector 10 extends from a needle holder of a syringe adapter 24, such as the syringe adapter 24 shown in FIG. 2. An inner surface of the needle holder may include a projection that cooperates with a body of the syringe adapter 24 to form a ratchet-type connection such that the needle holder is generally free to rotate relative to the body of the syringe adapter 24 in a first direction, but is generally restricted from such relative rotation when rotated in a second, opposite direction.

The body 12 of the connector 10 includes external threads 26 extending radially outward from the external surface 28 of the sidewall 20 and proceeding in a helical fashion from the distal end 16 to the proximal end 18 of the body 12. In the embodiment shown, the body 12 includes two external threads 26, although one or more threads may be provided. The external threads 26 each comprise a helical rib 30a, 30b defining a helical groove 32. The helical ribs 30a, 30b each include a root, flank portions 34, 36, and a crest 38. The crest 38 of the helical ribs 30a, 30b extends radially a distance from the external surface 28 of the sidewall 20. The helical ribs 30a, 30b may have any suitable cross-sectional shape, including, but not limited to, square, rounded, and trapezoidal. In the embodiment shown (FIGS. 2-7), the helical ribs 30a, 30b have a generally trapezoidal cross-section with the crest 38 positioned a distance from the external surface 28 of the sidewall 20 and substantially parallel to the external surface 28 of the sidewall 20. Two flank portions 34, 36 extend from the crest 38 inward toward the external surface 28 of the sidewall 20. The angle between the flank portions 34, 36 and the external surface 28 is greater than 90°, as is the angle between the flank portions 34, 36 and the crest 38 of the helical ribs 30a, 30b. The shape of the helical groove 32 is defined by the flank portions 34, 36 of the helical ribs 30a, 30b and the external surface 28 of the sidewall 20.

The helical ribs 30a, 30b are superimposed over at least one protrusion, such as a vertical rib 40, that extends radially from the external surface 28 of the sidewall 20 and axially from the proximal end 18 of the body 12 toward the distal end 16 of the body 12. In the embodiment shown in FIGS. 2-7, the connector 10 has two vertical ribs 40 positioned opposite from each on the body 12, although one or more vertical ribs 40 may be positioned at various positions around the body 12. For example, the connector 10 may include three or more circumferentially-spaced vertical ribs 40 with the geometry of the vertical ribs 40 being optimized to provide a desired amount of friction when secured to a mating connector. Due to the vertical position of the vertical rib 40, the superimposition of the helical ribs 30a, 30b over the vertical rib 40 results in portions of the vertical rib 40 being completely covered by the helical ribs 30a, 30b and portions of the vertical rib 40 being successively disposed within the helical groove 32.

Figure 5:
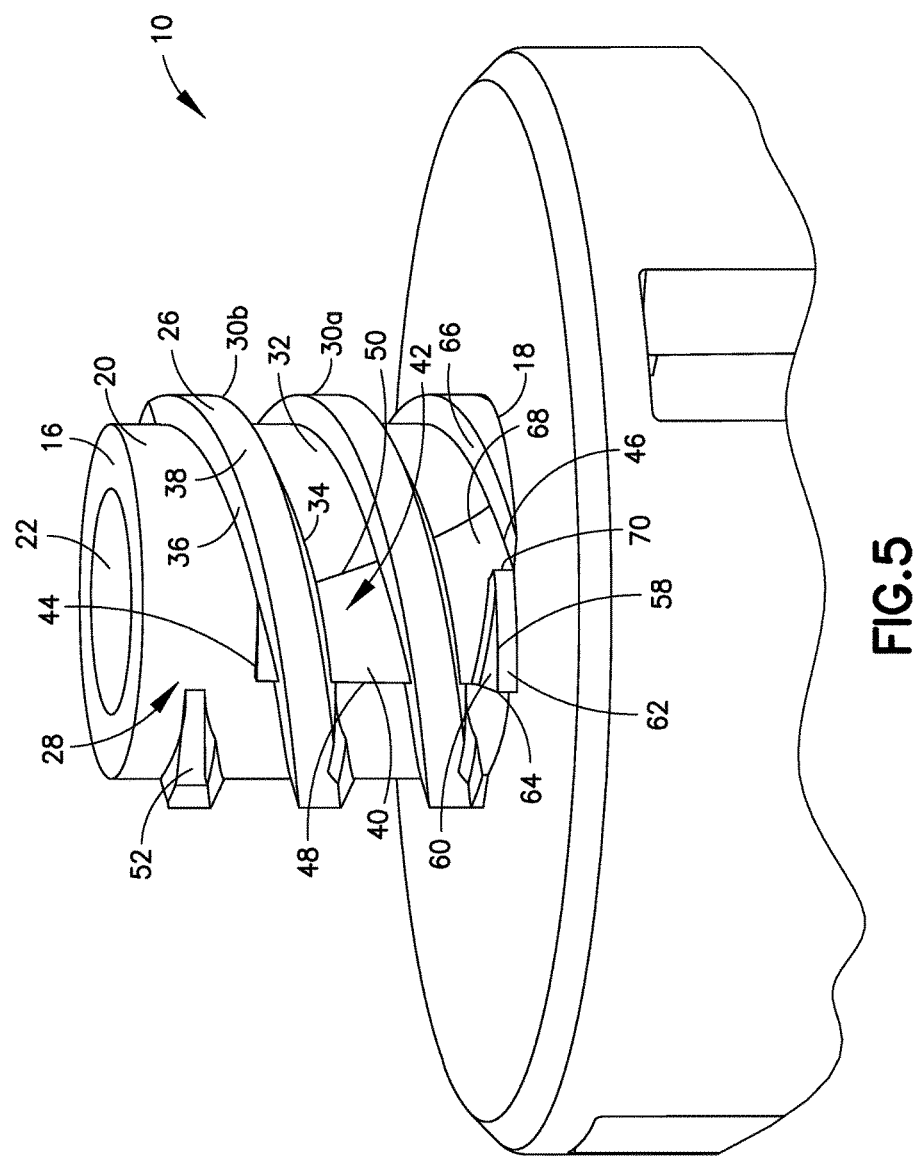
FIG. 5 is an enlarged right-side perspective view of the connector shown in FIG. 2 according to one embodiment of the present application.

The vertical rib 40 comprises an external surface 42, a distal wall 44, a proximal wall 46, a first side 48, and a second side 50 extending from the external surface 42 inward toward the exterior surface 28 of the sidewall 20 of the body 12 of the connector 10. While the external surface 42 and the sides 48, 50 of the vertical rib 40 may extend any axial distance from the proximal end 18 of the body 12, the distal wall 44 of the vertical rib 40 preferably does not extend past the distal-most portions 52 of the helical ribs 30a, 30b. The proximal wall 46 of the vertical rib 40 coincides with the proximal end 18 of the body 12 of the connector 10. The external surface 42 of the vertical rib 40 has a trapezoidal shape that tapers axially from the proximal wall 46 where the vertical rib 40 has the largest circumferential length to the distal wall 44 where the vertical rib 40 has the shortest circumferential length. The distal wall 44 is parallel to and has a smaller circumferential length than the proximal wall 46. The first side 48 and second side 50 extend between the distal wall 44 and the proximal wall 46 of the vertical rib 40 resulting in the external surface 42 of the vertical rib having a trapezoidal shape. While the first side 48 and second side 50 can extend from the distal wall 44 of the vertical rib 40 at any angle, in the embodiment shown in FIG. 5, the first side 48 extends at a 90° angle from the distal wall 44 and the second side 50 extends at an angle greater than 90° from the distal wall 44. As can be seen in FIG. 5, this results in each successive portion of the vertical rib 40 disposed within the helical groove 32 extending for a larger circumferential length within the helical groove 32 as the helical groove 32 approaches the proximal end 18 of the body 12 of the connector 10.

While the shape of the vertical rib 40 has been described and shown in the figures as trapezoidal, it can be appreciated by a person skilled in the art that the vertical rib 40 may take any suitable shape. In certain embodiments, the shape of the vertical rib 40 results in successive portions of the vertical rib 40 disposed within the helical groove 32 having successively larger circumferential lengths as the helical groove 32 approaches the proximal end 18 of the body 12 of the connector 10. For example, the vertical rib 40 may have an external surface 42 having a triangular, square, or rectangular shape. Alternatively, instead of the sides 48, 50 of the vertical rib 40 defining a generally continuous shape over which the helical ribs 30a, 30b are superimposed as shown in the figures, the side walls 48, 50 of the vertical rib 40 may extend in a stepwise manner from the distal wall 44 of the vertical rib 40 to the proximal wall 46 of the vertical rib 40.

Figure 3:
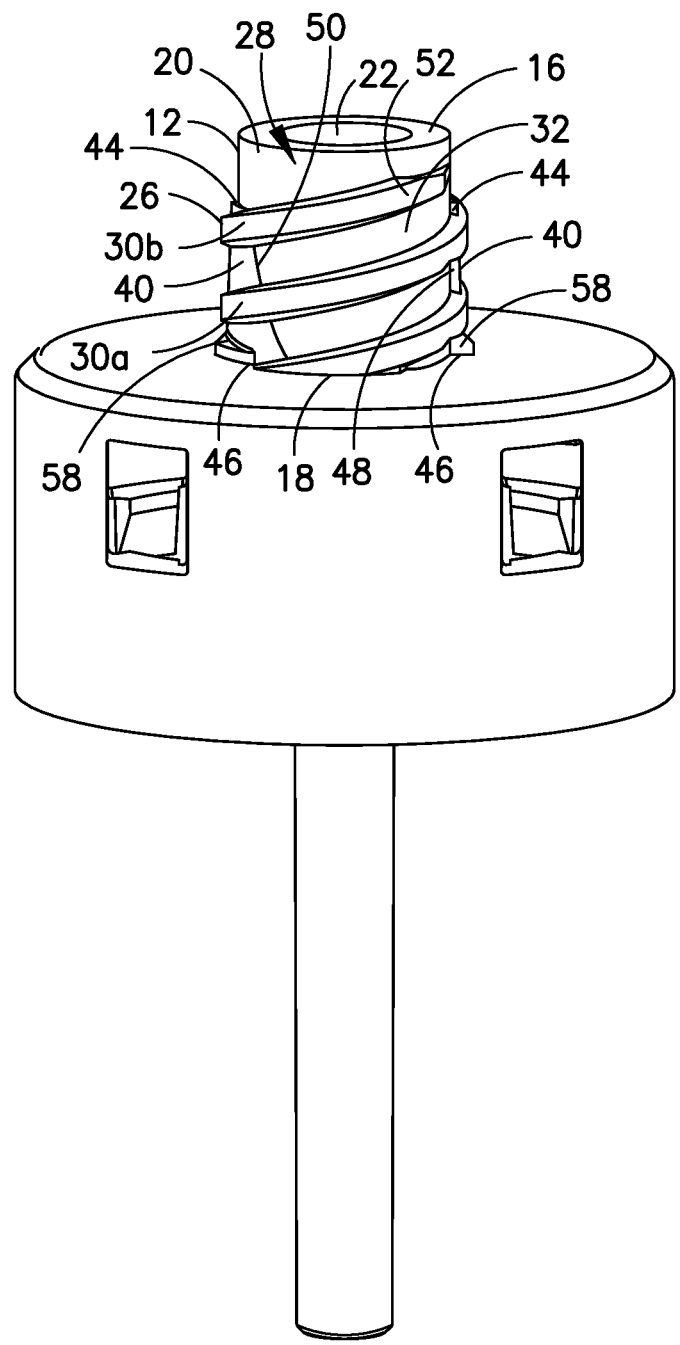
FIG. 3 is a rear perspective view of the connector shown in FIG. 2 according to one embodiment of the present application.
Figure 4:
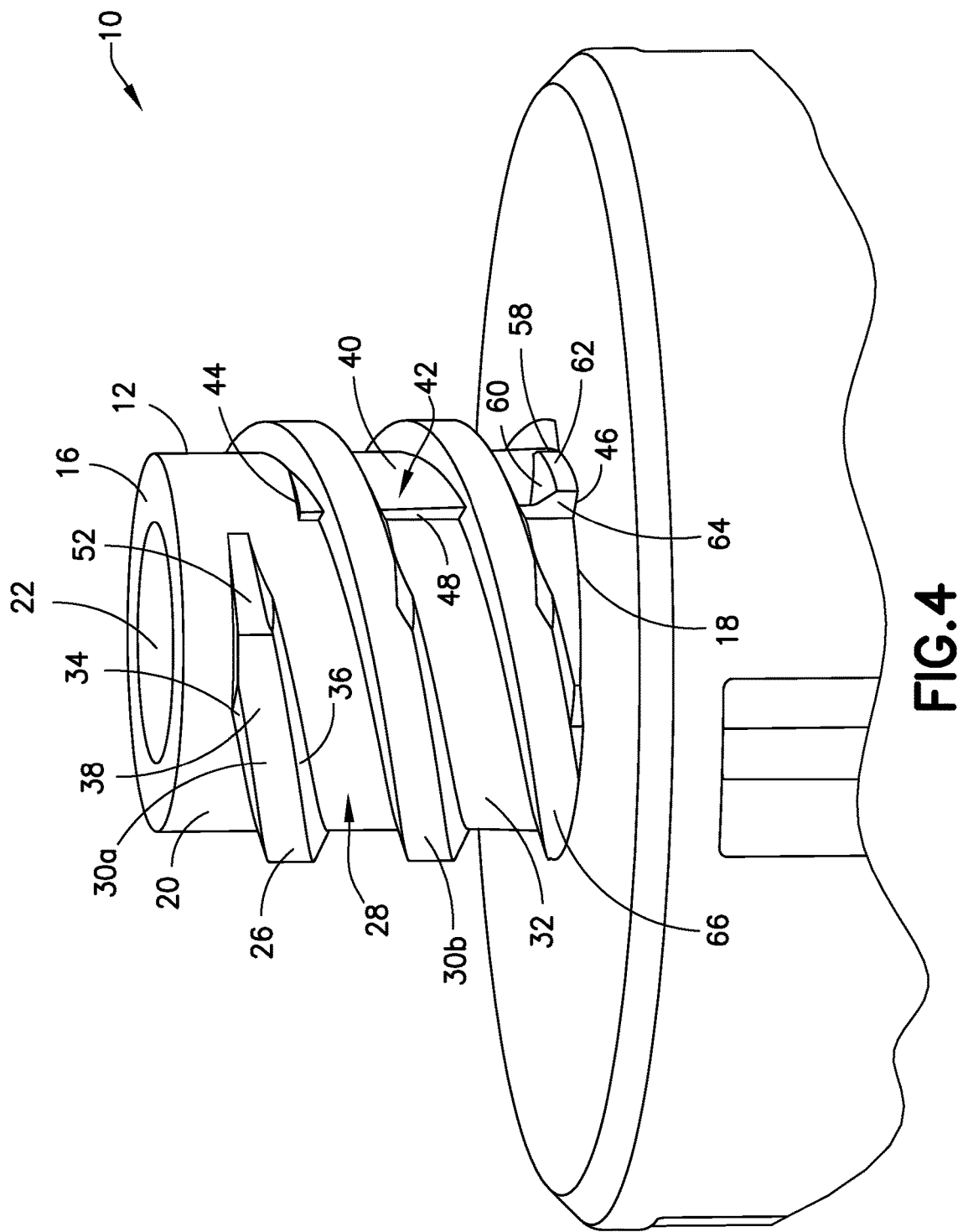
FIG. 4 is an enlarged front perspective view of the connector shown in FIG. 2 according to one embodiment of the present application.
Figure 6:
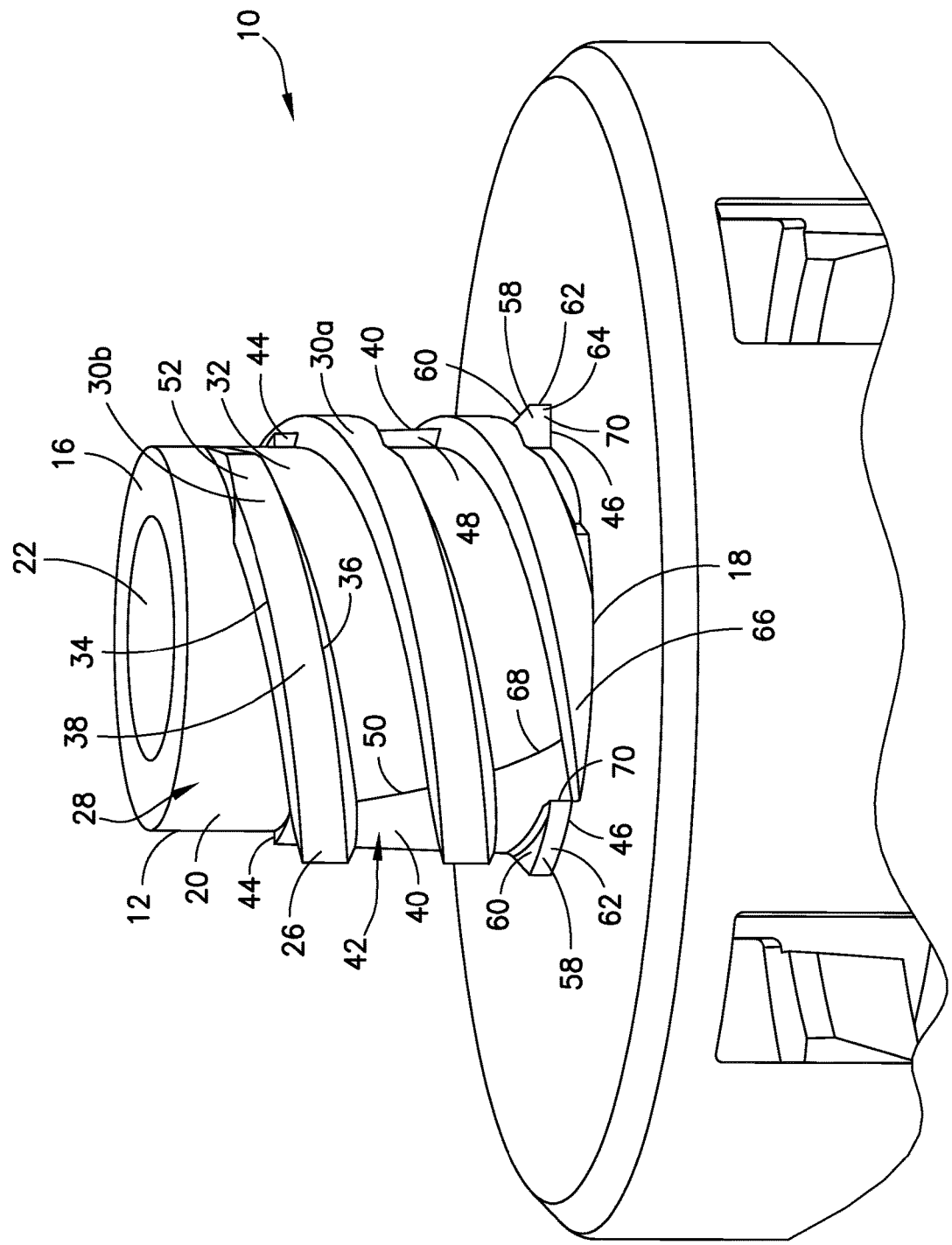
FIG. 6 is an enlarged rear perspective view of the connector shown in FIG. 2 according to one embodiment of the present application.

As can be seen in FIGS. 3 and 6, the radial height of the vertical rib 40 from the exterior surface 28 of the sidewall 20 of the body 12 tapers circumferentially from the first side 48 which takes the form of a vertical sidewall extending radially outward from the exterior surface 28 of the sidewall 20 of the body 12 to the second side 50 where the vertical rib 40 is substantially flush with the exterior surface 28 of the sidewall 20 of the body 12. Accordingly, the radial height of the vertical rib 40 increases from the second side 50 to the first side 48 of the vertical rib 40 such that the thinner or smaller portion of the vertical rib 40 is oriented on the higher side of a helix angle defined by the helical ribs 30a, 30b.

As can be seen in FIGS. 2-4, 6, and 7, the thickness of the vertical rib 40 from the exterior surface 28 of the sidewall 20 is also axially tapered from the proximal wall 46 to the distal wall 44. In FIGS. 2-4, 6, and 7, the first side 48 of the vertical rib 40 shows this taper. At the first side 48, the vertical rib 40 is at its maximum radial height from the external surface 28 of the sidewall 20 at the proximal wall 46 and the vertical rib 40 is at its minimum radial height from the external surface 28 of the sidewall 20 at the distal wall 44 of the vertical rib 40. Both the minimum and maximum radial heights of the vertical rib 40 from the external surface 28 of the sidewall 20 at the first side 48 are smaller than the radial height of the crest 38 of the helical ribs 30a, 30b from the external surface 28 of the sidewall 20. This axial taper results in the radial height of successive portions of the vertical rib 40 disposed within the helical groove 32 becoming successively larger as the helical groove 32 approaches the proximal end 18 of the body 12 of the connector 10. While the axial taper of the thickness of the vertical rib 40 has been described and shown as continuous, it can be appreciated by a person skilled in the art that the axial taper of the thickness of the vertical rib 40 may take any suitable path with the taper resulting in the radial height of successive portions of the vertical rib 40 disposed within the helical groove 32 becoming successively larger as the helical groove 32 approaches the proximal end 18 of the body 12 of the connector 10. For example, the axial taper of the thickness of the vertical rib 40 could proceed in a stepwise manner, instead of a continuous manner, from the proximal wall 46 of the vertical rib 40 to the distal wall 44 of the vertical rib 40. The taper may also ramp to a plateau.

As shown in FIGS. 2-7, a stop 58 may be included at the proximal wall 46 of the vertical rib 40. The stop 58 extends radially outward from the external surface 42 of the vertical rib 40 and comprises a top surface 60 and a sidewall 62 that extends from the top surface 60 to the proximal end 18 of the body 12 of the connector 10. The stop 58 has a first end 64 and a second end 70. The second end 70 of the stop 58 is adjacent the proximal-most end 66 of one of the helical ribs 30a, 30b and the stop 58 is generally disposed within the proximal-most end 68 of the helical groove 32. The top surface 60 and the sidewall 62 of the stop 58 taper circumferentially from the first end 64 to the second end 70 of the stop 58 such that the first end 64 of the stop 58 has a radial height from the external surface 42 of the vertical rib 40 that is larger than the radial height of the second end 70 from the external surface 42 of the vertical rib 40. The second end 70 of the stop 58 may be substantially flush with the external surface 42 of the vertical rib 40. This taper causes the top surface 60 of the stop 58 to take the shape of a triangle and the stop 58 has an overall wedge shape in the embodiment shown in FIG. 5.

While the stop 58 has been described and is shown in the figures as having a circumferential taper and a top surface with a triangular shape, it can be appreciated by a person skilled in the art that the circumferential taper of the stop 58 and the resulting top surface 60 may take any suitable path and shape as long as the radial height of the stop 58 from the exterior surface 42 of the vertical rib 40 increases from the first end 64 of the stop 58 to the second end 70 of the stop 58.

The connector 10 is configured to be secured to and mate with a mating connector 14 that includes a body 72 having a distal end 74, a proximal end 76, and a generally cylindrical sidewall 78 extending between the distal end 74 and the proximal end 76 and defining a central lumen 80. The mating connector 14 may be a male luer-lock connector, although other suitable mating connectors may be utilized. The proximal end 76 of the body 72 of the mating connector 14 may be attached directly to a first fluid container or may extend from an additional connection portion that connects directly to the fluid container to provide a fluid connection between the first fluid container and the central lumen 80 of the body 72 of the mating connector 14. In the embodiment shown in FIGS. 1 and 7, the body 72 of the mating connector 14 extends from a syringe such as the one shown in FIG. 1.

The body 72 of the mating connector 14 includes internal threads 84 extending radially inward from the internal surface 86 of the sidewall 78 and proceeding in a spiral fashion from the distal end 74 to the proximal end 76 of the body 72. The body 72 may be provided with one or more internal threads 84. In the embodiment shown in FIG. 7, the body 72 of the mating connector 14 is provided with two internal threads 84. The internal threads 84 each comprise a helical rib 88a, 88b that together define helical groove 90. The helical ribs each include a root, flank portions 92, 94, and a crest 96. The helical ribs 88a, 88b extend radially a distance from the internal surface 86 of the sidewall 78. The helical ribs 88a, 88b may have any suitable cross-sectional shape, including, but not limited to, square, rounded, and trapezoidal. The helical ribs 88a, 88b and helical groove 90 are shaped and sized to engage the opposing helical ribs 30a, 30b and helical groove 32 of the body 12 of the connector 10 so that the body 72 of the connector 14 can be threaded onto the body 12 of the connector 10 and tightened to form the connection.

Figure 7:
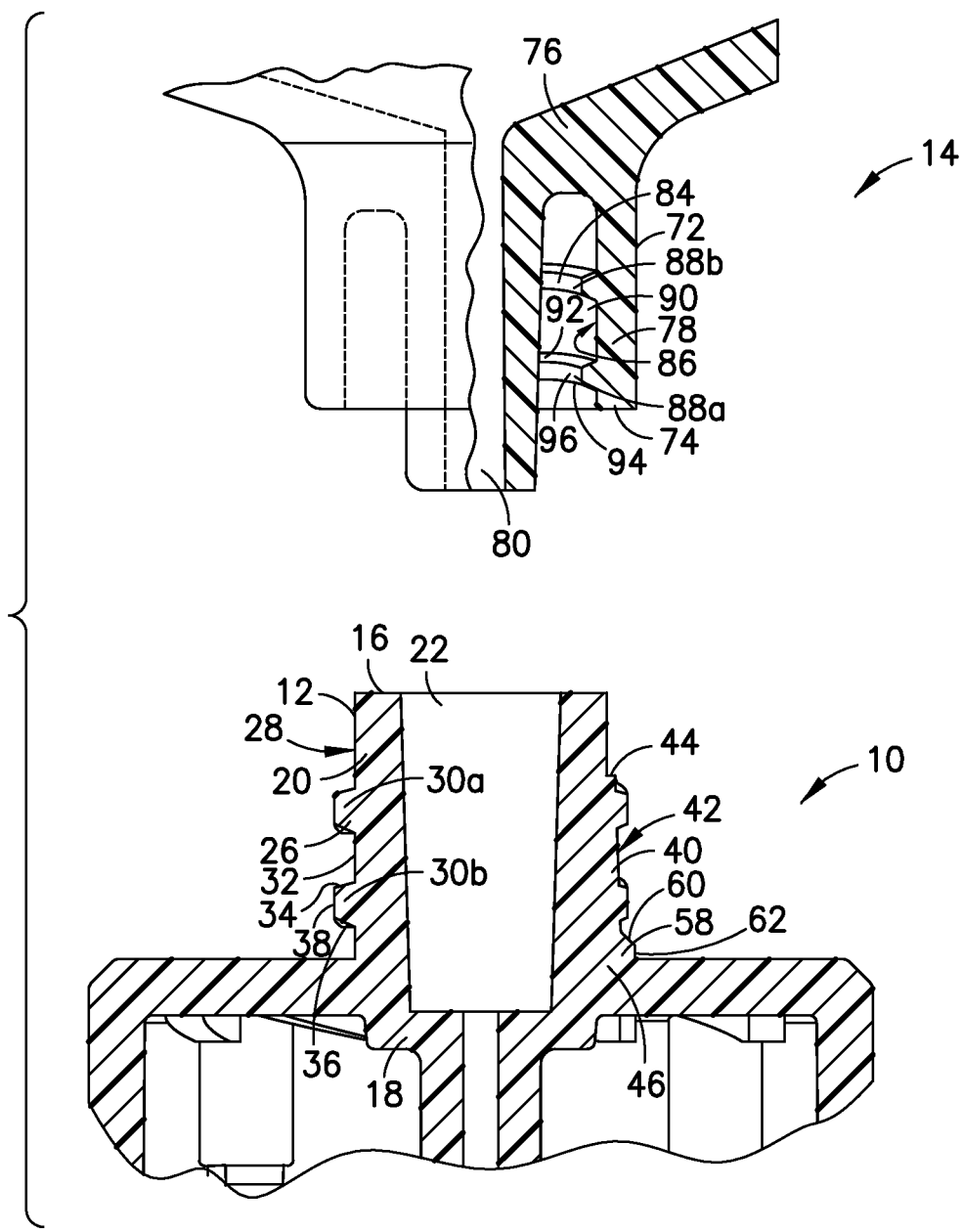
FIG. 7 is a partial cross-sectional view of the connector shown in FIG. 2 and a mating connector in a disconnected state according to one embodiment of the present application.

In the embodiment shown in FIG. 7, the helical ribs 88a, 88b have a generally trapezoidal cross-section with the crest 96 a distance from the internal surface 86 of the sidewall 78 and substantially parallel to the internal surface 86 of the sidewall 78. Two flank portions 92, 94 extend from the crest 96 inward toward the internal surface 86 of the sidewall 78. The angle between the flank portions 92, 94 and the internal surface 86 is greater than 90° as is the angle between the flank portions 92, 94 and the flank portion 92, 94 of the helical ribs 88a, 88b. The shape of the helical groove 90 is defined by the flank portions 92, 94 of the helical ribs 88a, 88b and the internal surface 86 of the sidewall 78. In the embodiment shown in FIG. 7, the helical groove 90 has a trapezoidal shape.

When a user of the connector 10 desires to make the connection, the mating connector 14 is threaded onto the connector 10, such that the helical ribs 88a, 88b of the mating connector 14 engage the helical groove 32 of the connector 10 and the helical ribs 30a, 30b of the connector 10 engage the helical groove 90 of the mating connector 14. As the user continues to advance the mating connector 14 onto the connector 10, the distal wall 44 of the vertical rib 40 of the connector 10 engages the helical ribs 88a, 88b of the mating connector 14 resulting in increased friction between the connector 10 and the mating connector 14. The user must then apply increased torque to continue to advance the mating connector 14 onto the connector 10. This provides an indication to the user that the connection is being made and that the connection is being tightened. As the user continues to advance the mating connector 14 onto the connector 10, a portion of the vertical rib 40 positioned closer to the proximal end 18 of the connector 10 engages the helical ribs 88a, 88b of the mating connector 14. As the vertical rib 40 increases in radial height as it extends from the distal wall 44 to the proximal wall 46, this portion of the vertical rib 40 has a larger circumferential width within the helical groove 32 of the connector 10 and a larger maximum radial height than the distal wall 44 of the vertical rib 40 as described above. This results in even more increased friction between the connector 10 and the mating connector 14 and provides further indication that the connection is being tightened. This continues until the distal-most end of the helical rib 88a, 88b of the mating connector 14 contacts the stop 58 at the proximal end 18 of the body 12 of the connector 10. As the user continues to apply torque to the mating connector 14, the distal-most end of the helical rib 88a, 88b of the mating connector 14 is increasingly engaged in a wedging manner by the stop 58 due to its circumferential taper to prevent further tightening of the mating connector 14.

Also, the circumferential taper of the radial height of the vertical rib 40, i.e., the decrease in radial height from the first side 48 to the second side 50 of the vertical rib 40, acts to resist disconnection of the connector 10 with the mating connector 14. The circumferential taper from the first side 48 of the vertical rib 40 to the second side 50 of the vertical rib 40 allows the helical ribs 88a, 88b to advance over the vertical rib 40 as the mating connector 14 is threaded onto the connector 10. However, the first side 48 of the vertical rib 40, which takes the form of a sidewall, that extends from the exterior surface 28 of the sidewall 20 of the body 12 of connector 10 and acts as a barb to resist disconnection. In other words, the second side 50 of the vertical rib 40 is about flush with the sidewall 20 of the body 12, which allows the mating connector 14 to be threaded onto the connector 10. The vertical rib 40 increases in radial height as it extends circumferentially to the first side 48 of the vertical rib 40 with the first side 48 defining a sidewall that will engage and bite into the mating connector 14 if a user attempts to unthread the mating connector 14 from the connector 10.

Thus, the engagement of both the vertical rib 40 and the stop 58 of the connector 10 with the helical rib 88a, 88b of the mating connector 14 results in gradually increasing friction as the mating connector 14 is advanced onto the connector 10. This gradually increasing friction and corresponding increase in torque to make the connection provide an indication to the user that the connection between the connector 10 and the mating connector 14 is being secured. The increased feeling of tightness that is transferred to the user encourages the user to stop applying torque when the connection is tight and discourages over-tightening of the connection which can result in breakage of the mating connector 14 or the connector 10. In addition, the increased friction and circumferential taper of the vertical rib 40 make the connection more resistant to disconnection than a connection that merely utilizes corresponding internal and external threads and the inherent friction properties of the material.

While the discussion and figures have described the vertical rib 40 and the stop 58 in conjunction with the body 12 of the connector 10, it can be appreciated by a person skilled in the art that the same result may be achieved in the same manner by incorporating the vertical rib 40 and the stop 58 into the threaded portion of the mating connector 14.

The protrusions disposed in the helical grooves have been described and shown as being portions of a vertical rib, the protrusions may take any shape and form with the protrusions increasing in circumferential width as the distance between the protrusion and the distal end of the portion increases and/or the individual protrusions taper circumferentially. The protrusions may also increase in radial height from the sidewall as the distance between the protrusion and the distal end of the portion increases. This allows for each step of frictional increase provided by contact of the helical rib with a protrusion as the mating connector is advanced onto the connector to be larger than the frictional increase provided by contact of the helical rib with the previous protrusion creating an ever tighter connection and giving the user an ever increasing sense of tightness. Alternatively, or in addition, the protrusions may taper circumferentially.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

The invention claimed is:

1. A medical connector comprising:
   a body having a distal end, a proximal end, and a sidewall extending between the distal end and the proximal end;
   a helical thread extending radially outward from a surface of the sidewall; and
   at least one protrusion extending radially outward from the surface of the sidewall, the at least one protrusion having a proximal end and a distal end, the at least one protrusion extending axially along the sidewall between the helical thread,
   wherein a radial height of the at least one protrusion from the surface of the sidewall tapers axially from the proximal end of the at least one protrusion to the distal end of the at least one protrusion.

2. The medical connector according to claim 1, wherein a circumferential width of the at least one protrusion increases along a distance from the distal end of the body of the connector to the proximal end of the body of the connector.

3. The medical connector according to claim 1, wherein the helical thread is superimposed over the at least one protrusion, and wherein the at least one protrusion comprises a vertical rib.

4. The medical connector according to claim 3, wherein the vertical rib has a circumferential width that tapers axially from the proximal end of the vertical rib where the vertical rib has the widest circumferential width to the distal end of the vertical rib where the vertical rib has the narrowest circumferential width.

5. The medical connector according to claim 1, wherein the at least one protrusion further comprises a first side and a second side, wherein the at least one protrusion from the surface of the sidewall tapers circumferentially from the first side of the at least one protrusion to the second side of the at least one protrusion, and wherein the second side of the at least one protrusion is substantially flush with the sidewall.

6. The medical connector according to claim 1, wherein a maximum radial height of the at least one protrusion from the surface of the sidewall of the body of the connector is less than a radial height of the helical thread of the connector from the sidewall.

7. The medical connector according to claim 1, wherein a radial height of the at least one protrusion from the surface of the sidewall of the body of the connector increases as a distance from the distal end of the connector increases.

8. The medical connector according to claim 1, further comprising a stop extending radially outward from the surface of the sidewall at the proximal end of the body of the connector.

9. The medical connector according to claim 8, wherein a radial height of the stop from the sidewall tapers circumferentially from a first end to a second end of the stop such that the first end of the stop has a radial height from the surface of the sidewall that is larger than a radial height of the second end from the surface of the sidewall.

10. The medical connector according to claim 9, wherein the second end of the stop is adjacent a proximal-most end of the helical thread.

11. The medical connector according to claim 1, wherein the at least one protrusion comprises a vertical rib, and
   wherein the helical thread comprises first and second helical ribs, the vertical rib extending through the first and second helical ribs.

12. The medical connector according to claim 11, wherein the vertical rib is divided into a plurality of sections by the first and second helical ribs of the helical thread.

13. A medical connector comprising:
   a body having a distal end, a proximal end, and a sidewall extending between the distal end and the proximal end;
   a helical thread extending radially outward from a surface of the sidewall; and
   at least one protrusion extending radially outward from the surface of the sidewall, the at least one protrusion having a proximal end and a distal end, the at least one protrusion extending axially along the sidewall between the helical thread,
   wherein a circumferential width of the at least one protrusion is larger at the proximal end of the at least one protrusion than the circumferential width of the at least one protrusion at the distal end of the at least one protrusion, and
   wherein a radial height of the at least one protrusion from the surface of the sidewall tapers axially from the proximal end to the distal end.

14. The medical connector according to claim 13, wherein the circumferential width of the at least one protrusion increases as a distance from the distal end of the body of the connector to the at least one protrusion increases.

15. The medical connector according to claim 13, wherein the helical thread is superimposed over the at least one protrusion, and wherein the at least one protrusion comprises a vertical rib.

16. The medical connector according to claim 13, wherein a maximum radial height of the at least one protrusion from the surface of the sidewall of the body of the connector is less than a radial height of the helical thread of the connector from the sidewall.

17. The medical connector according to claim 13, wherein a radial height of the at least one protrusion from the surface of the sidewall of the body of the connector increases as a distance from the distal end of the body of the connector increases.

18. A method of connecting two fluid containers comprising:

providing a connector having a helical thread extending radially outward from a surface of the connector, and a mating connector comprising a helical thread extending radially outward from a surface of the mating connector, the connector including at least one protrusion extending radially outward from the surface of the connector, the at least one protrusion tapering axially from a proximal end of the at least one protrusion to a distal end of the at least one protrusion;

engaging the helical thread of the mating connector with the helical thread of the connector;

advancing the mating connector onto the connector by rotating the mating connector; and engaging the at least one protrusion with the mating connector such that the friction between the connector and the mating connector is increased when the at least one protrusion of the connector contacts the helical thread of the mating connector as the mating connector is advanced onto the connector, the at least one protrusion is sized and positioned such that the increase in friction provided by contact with each successive portion of the at least one protrusion is greater than the increase in friction provided by a previously contacted portion of the at least one protrusion.

19. The method according to claim 18, wherein a first portion of the at least one protrusion that first contacts the helical thread of the mating connector has a narrower circumferential width than a second portion of the at least one protrusion that is subsequently contacted by the helical thread of the mating connector as the mating connector is advanced on the connector.

20. The method according to claim 18, wherein a first portion of the at least one protrusion that first contacts the helical thread of the mating connector has a maximum radial height from a surface of the connector that is smaller than a maximum radial height from a surface of the connector of a second portion of the at least one protrusion that is subsequently contacted by the helical thread of the mating connector as the mating connector is advanced onto the connector.

21. The method according to claim 18, further comprising:

engaging a stop with the mating connector to stop advancement of the mating connector onto the connector.

* * * * *